United States Patent
Yang

(10) Patent No.: US 7,491,319 B1
(45) Date of Patent: Feb. 17, 2009

(54) INSPECTING APPARATUS WITH EDDY CURRENT INSPECTION

(75) Inventor: Ming-Liau Yang, Gangshan Township, Kaohsiung County (TW)

(73) Assignee: Te Hung En Enterprise Co., Ltd., Kaohsiung County (TW)

( * ) Notice: Subject to any disclaimer, the term of this patent is extended or adjusted under 35 U.S.C. 154(b) by 0 days.

(21) Appl. No.: 12/076,285

(22) Filed: Mar. 17, 2008

(51) Int. Cl.
*C22B 11/10* (2006.01)
(52) U.S. Cl. ........................................ 209/57; 209/929
(58) Field of Classification Search ................. 209/929, 209/567, 571, 559, 900; 198/339.1
See application file for complete search history.

(56) References Cited

U.S. PATENT DOCUMENTS

| | | | | |
|---|---|---|---|---|
| 3,539,006 A | * | 11/1970 | Pajak et al. .................. | 209/555 |
| 4,230,987 A | * | 10/1980 | Mordwinkin ................ | 324/236 |
| 4,558,775 A | * | 12/1985 | LaBarge et al. ............. | 194/208 |
| 4,891,986 A | * | 1/1990 | Teagle .......................... | 73/634 |
| 4,905,842 A | * | 3/1990 | Habele et al. ................ | 209/557 |
| 5,056,016 A | * | 10/1991 | Dobler et al. ................ | 324/232 |
| 5,165,551 A | * | 11/1992 | Frost ............................ | 209/538 |
| 5,423,492 A | * | 6/1995 | Willis ........................... | 241/81 |
| 5,666,051 A | * | 9/1997 | Junker et al. ................. | 324/209 |
| 5,823,356 A | * | 10/1998 | Goodrich et al. ............. | 209/601 |
| 6,039,645 A | * | 3/2000 | Mazur .......................... | 453/10 |
| 6,878,724 B2 | * | 4/2005 | Meerpoel et al. ............. | 514/317 |
| 2004/0022427 A1 | * | 2/2004 | Yang et al. ................... | 382/141 |

\* cited by examiner

*Primary Examiner*—Patrick Mackey
*Assistant Examiner*—Michael E. Butler
(74) *Attorney, Agent, or Firm*—Rosenberg, Klein & Lee

(57) ABSTRACT

The present invention pertains to an inspecting apparatus with eddy current inspection introducing the objects in sequence into the eddy current probe by the turntable; further, by means of the braking assembly and the dispensing system of the probe, the objects are able to be detected under the nondestructive inspection and precisely determined qualities thereof. Additionally, the turntable can have a camera disposed thereon for preceding examinations and selections so that the probe only needs to detect the retaining flawless objects, and which promotes the precise inspection and increases the detecting speed.

3 Claims, 6 Drawing Sheets

INSPECTING APPARATUS WITH EDDY CURRENT INSPECTION

BACKGROUND OF THE INVENTION

1. Field of the Invention

The present invention relates to an inspecting apparatus, more particularly to an inspecting apparatus with eddy current inspection.

2. Description of the Related Art

Referring to FIG. 1, a conventional inspecting apparatus 1 mainly consists of a base 11, an inlet feeding system 12 for transporting objects 2 (for instance of screws or nuts), an inspecting rail 13 attached to the feeding system 12, an eddy current machine 14 disposed on the rail 13, and a determining device 15 communicating with the eddy current machine 14. By the concatenation of the above elements, the objects 2 are continuously introduced into the rail 13 by the feeding system 12 and inspected by passing through the eddy current machine 14. The eddy current machine 14 thus transmits the signals to the determining device 15 for the detail analyses.

In operation, the conventional invention simply carries on detecting the object by the visual inspection, e.g. the external and internal cracks; however, the object 2 additionally requires appropriative apparatuses (not shown in the figure) for detecting other items thereof, for instance of the thread diameter or the pitch measurements, so that the detection of the object would be interrupted and the detecting speed thus is suspended while moving the object 2 to other apparatuses for multiple inspections, thus affecting the detecting speed. Moreover, the inlet feeding system 12 is not able to properly space the objects 2 apart while introducing them into the rail 13, which would facilely result in that the object thrusts to its front detecting object in time of feeding, thus affecting the captures signals of the eddy current machine 14. Therefore, the determining device 15 may still have higher possibility of the inaccurate inspection.

SUMMARY OF THE INVENTION

The object of the present invention is to provide an inspecting apparatus with eddy current inspection which is conducive to obtain rapid speed detection and increase the inspecting efficiency.

The inspecting apparatus with eddy current inspection in conformity with the present invention essentially comprises a determining device, an inlet conveyer system, a turntable connecting to the inlet conveyer system, a shield board surrounding the turntable, an outlet conveyer system disposed beside the turntable and an eddy current probe engaged to the outlet conveyer system; wherein, the eddy current probe has a detecting entrance, a detector connected to the determining device, and a braking assembly and a dispensing system respectively disposed on the entrance. Therefore, the object is able to be sequentially introduced into the detecting entrance by assistance of the turntable and the outlet conveyer system, then detected under a nondestructive inspection and analyzed by the determining device; further the dispensing system sorts the object into defective or non-defective according to the analyzed record. Furthermore, the present apparatus can also have initial examinations and selections in the range from the turntable to the outlet conveyer system so that the probe only needs to detect those retaining flawless objects for preciously ensuring the inspecting qualities and increasing the detecting speed.

The advantages of the present invention over the known prior arts will become more apparent to those of ordinary skilled in the art by reading the following descriptions with the relating drawings.

DETAILED DESCRIPTION OF THE PREFERRED EMBODIMENTS

Figure 1:
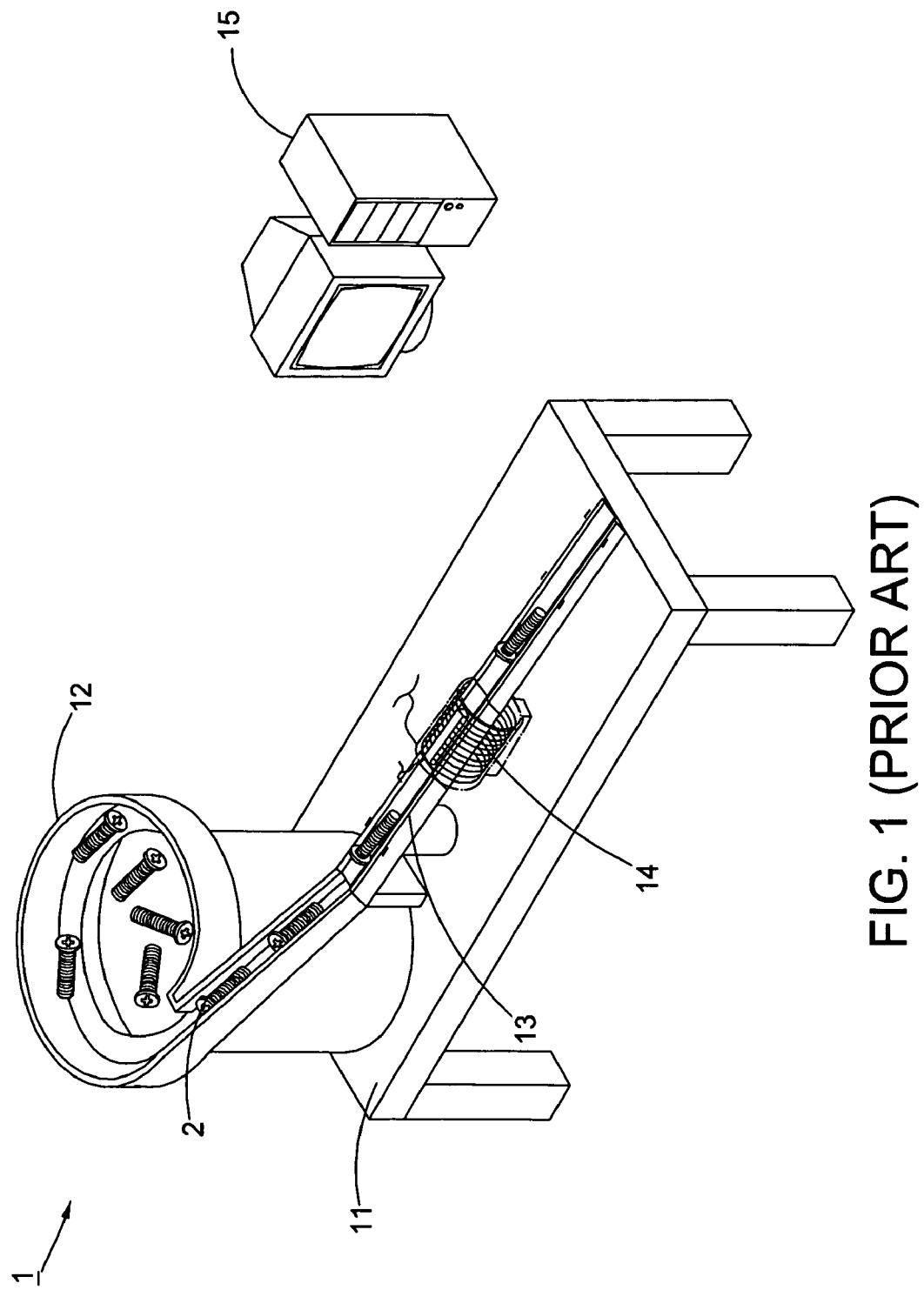
FIG. 1 is a perspective view showing a conventional invention.

Before describing in greater detail, it should note that the like elements are denoted by the similar reference numerals throughout the disclosure.

Figure 2:
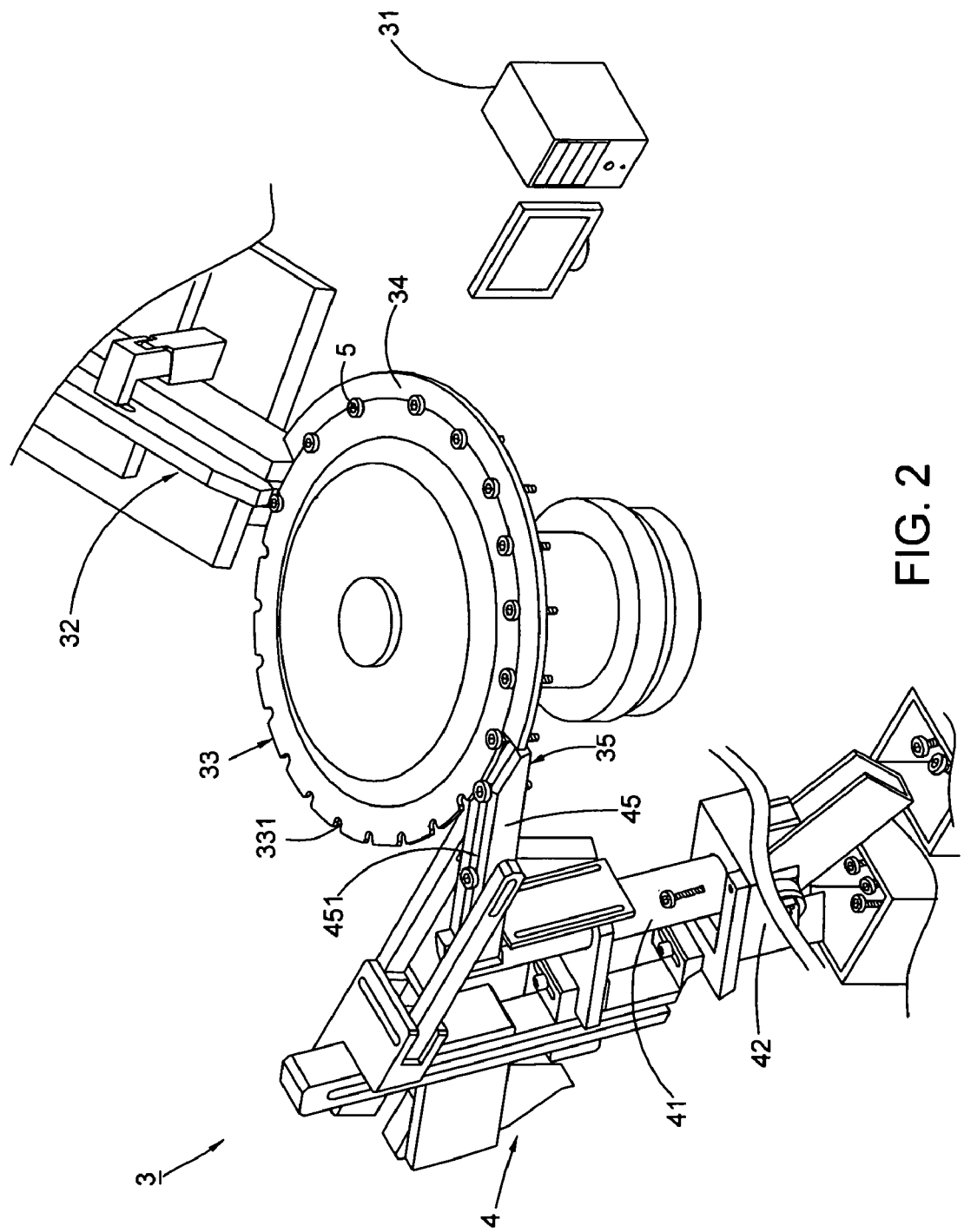
FIG. 2 is a perspective view showing a first preferred embodiment of the present invention.

Referring to FIG. 2, an inspecting apparatus 3 with eddy current inspection of the first preferred embodiment comprises a determining device 31, an inlet conveyer system 32 for orientating and aligning objects 5 (for instance of screws or nuts), a turntable 33 connecting to an exit of the inlet conveyer system 32, a shield board 34 surrounding the turntable to prevent drops of the objects 5, an outlet conveyer system 35 disposed at one side of the turntable 33, and an eddy current probe 4 engaged to the outlet conveyer system 35 and communicating with the determining device 31; wherein, the turntable 33 includes a plurality of cutout grooves 331 spaced around an outer periphery thereof to receive and position the objects 5 therein.

Figure 3:
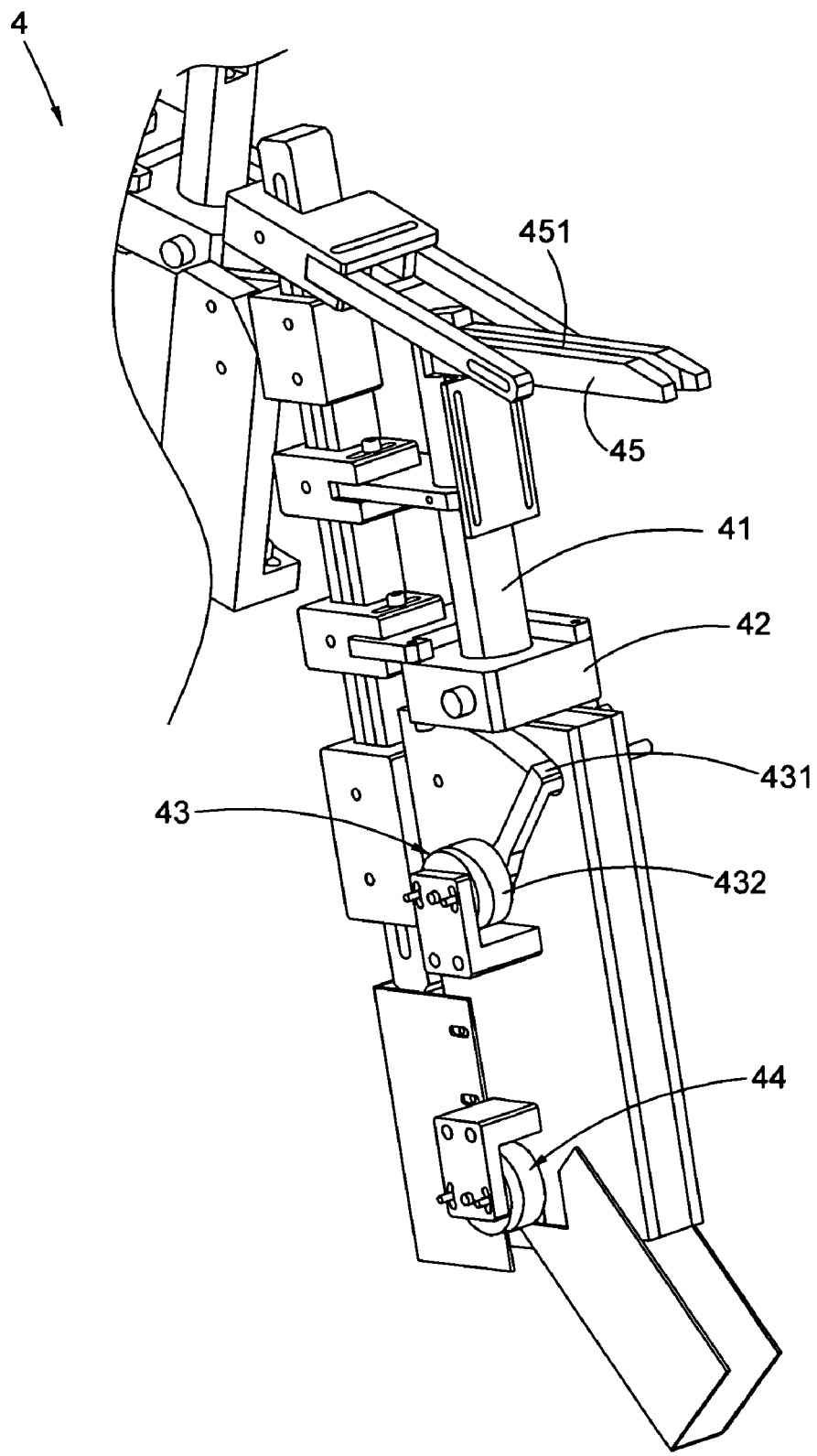
FIG. 3 is a partial enlarged view showing the eddy current probe of the first embodiment.
Figure 4:
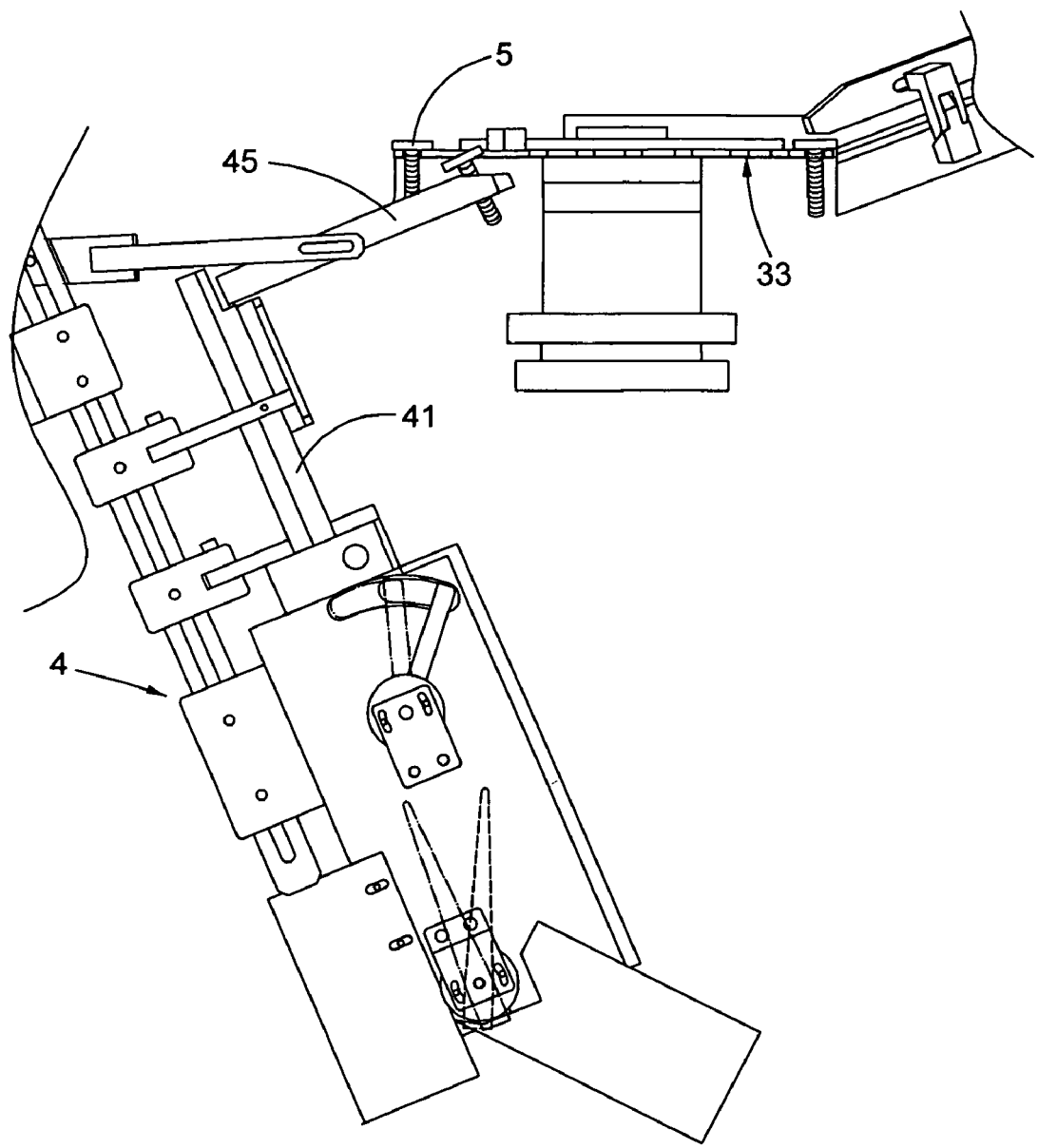
FIG. 4 is a side view showing the first embodiment.
Figure 5:
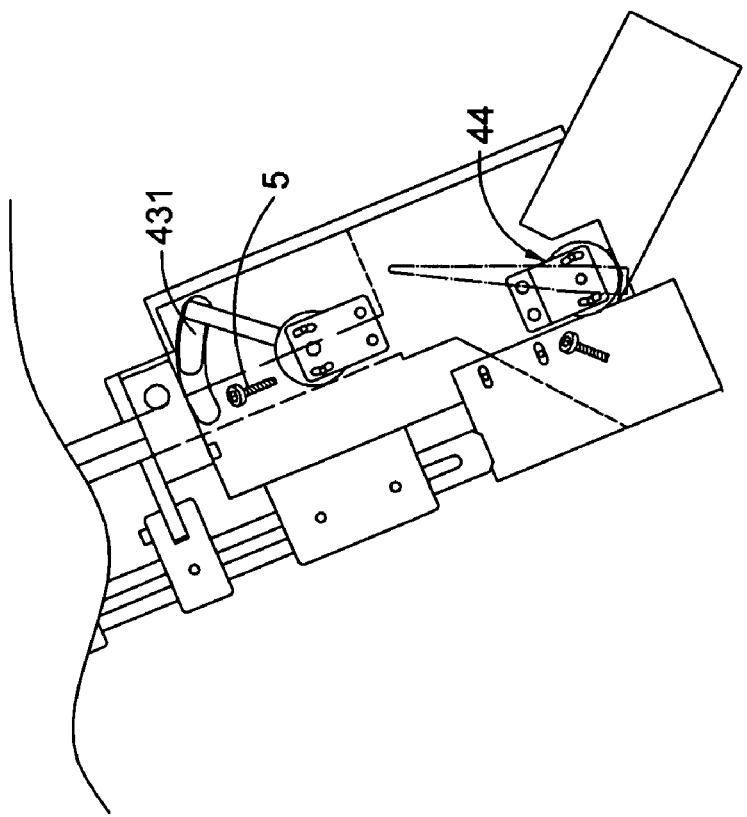
FIG. 5 and FIG. 6 are schematic views showing the eddy current probe in time of operation.

Still further, referring to FIGS. 2 and 3, the eddy current probe 4 provides with a detecting entrance 41 for the objects 5 traveling therein, a detector 42 disposed on an outer circumference of the detecting entrance 41 and communicating with the determining device 31, and a braking assembly 43 and a dispensing system 44 respectively mounted on the detecting entrance 41; wherein, the braking assembly 43 has a power motor 432, and a braking rod 431 driven by the power motor 432 and laterally mounted through the detecting entrance 41 for resting the objects 5. Additionally, the dispensing system 44 is located below the braking assembly 43, whereby the objects 5 are able to temporarily contact with the detector 42 under a nondestructive inspection and then be sorted into defectives or non-defectives based on analyses of the determining device 31. As shown in FIG. 4, the outlet conveyer system 35 is adopted to include two guiding rails 45 and a channel 451 formed therebetween; that is, the two guiding rails 45 have their ends disposed below the turntable 33 and their other ends contacted with the inspecting entrance 41, so that the objects 5 are able to be sequentially transported from the turntable 33 to the eddy current probe 4.

Figure 6:
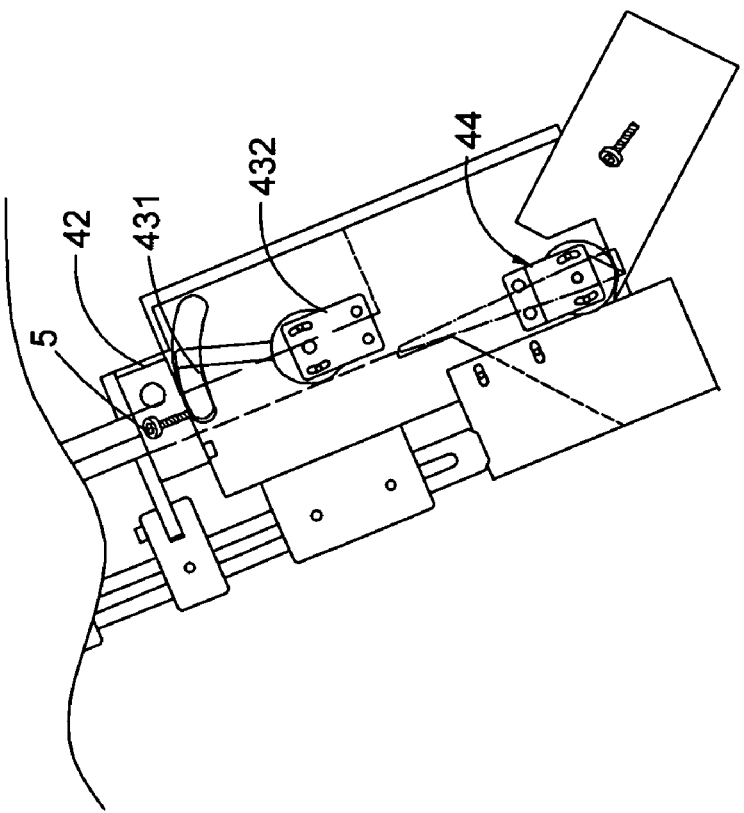

While in detecting, referring to FIGS. 2 to 5, each object 5 is initially introduced into the cutout groove 331 by the inlet conveyer system 32, so that the turntable 32 can equidistantly transport the objects 5. Further, the output conveyer system 35 propels the object 5 to sequentially enter into the inspecting entrance 41 through the guiding rail 45 so as to prevent the shoving among the objects 5. Subsequently, the braking rod 431 driven by the power motor 432 initially blocks each object 5 (shown in FIG. 5) and makes it contact with the detector 42 for a nondestructive inspection. The detector 42 receives the detecting signals and transmits them to the determining device 31 for analyzing the quality of the object 5. Finally, the braking rod 431 frees the object 5 and passes it through the dispensing system 44 (shown in FIG. 6) for sorting the object 5 into defective or non-defective according to the analyzed record, thus achieving high speed detection and increasing the inspecting efficiency.

Figure 7:
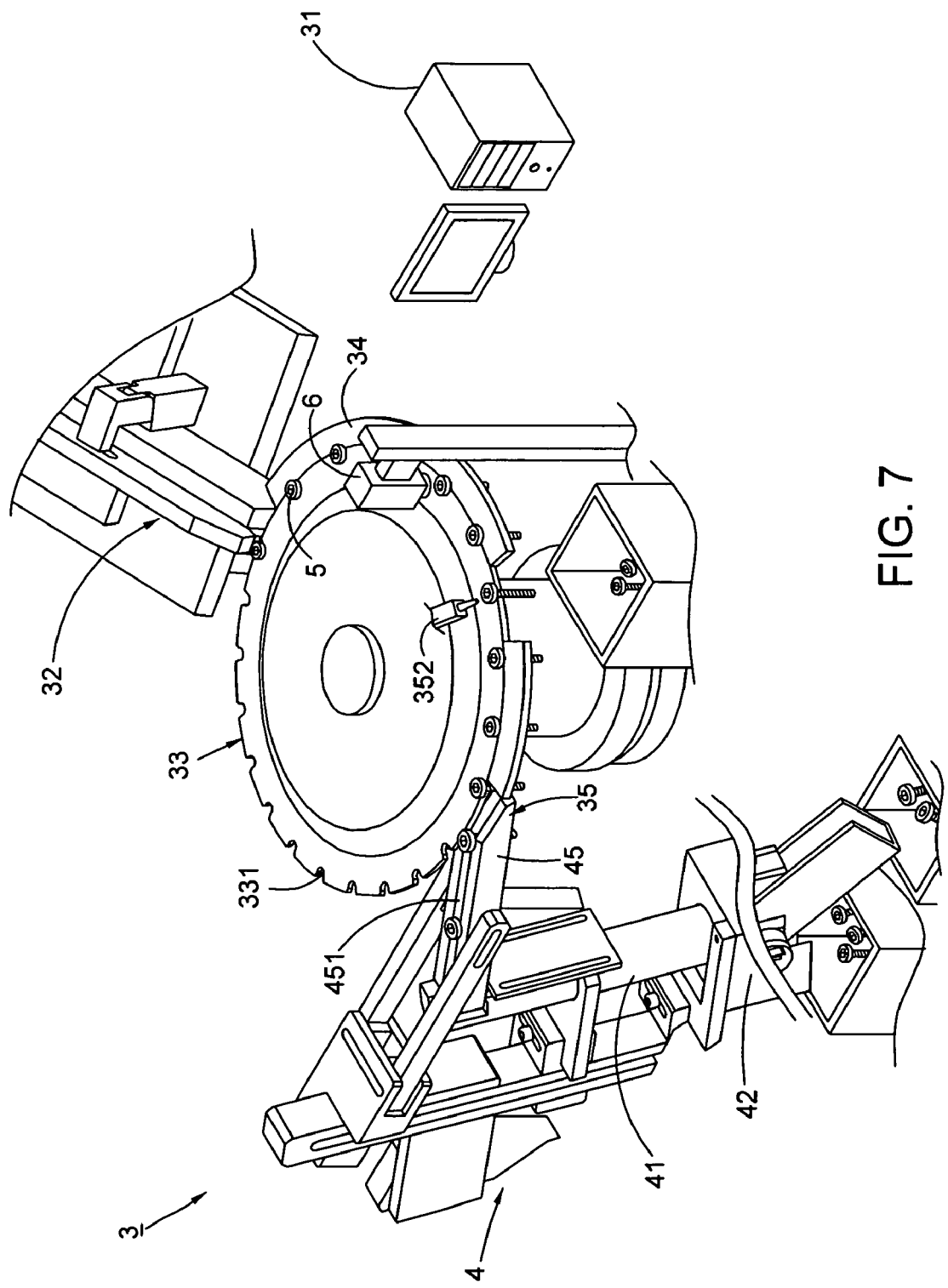
FIG. 7 is a perspective view showing another preferred embodiment of the present invention.

Referring to FIG. 7, another preferred embodiment of the present invention still comprises a determining device 31, an eddy current probe 4, an inlet conveyer system 32, a turntable 33 with a shield board 34 disposed therearound, and an outlet conveyer system 35. Particularly, a camera 6 is mounted on the turntable 33 and electrically connected to the determining device 31; further, the outlet conveyer system 35 includes a pusher 352 separately disposed on the turntable 33 so as to initially discard the defective and malformed object 5. The pusher 352 is adopted as a jet of high pressure gas in this embodiment.

Still referring to FIG. 7, the object 5 is firstly introduced into cutout groove 331 and sequentially transported by the turntable 33. The object 5 is then moved below the camera 6 for providing precedence to the optical detection, e.g. receiving the surface signal thereof, and the camera 6 transmits the signal to the determining device 31 to attain the initial analysis. Immediately, the outlet conveyer system 35 sorts the objects 5 into defectives and non-defectives based on the analysis, namely the pusher 352 directs its jet at the flaw object 5 to deviate it from the turntable 33 and keeps the retaining flawless objects 5 staying at their positions, the two guiding rails 45 thus guide the flawless objects 5 in sequence into the eddy current probe 4 along the channel 451, thereby preventing the problem of shoving. In this manner, the flawless objects 5 is initially selected by the camera 6 and detected once again under the nondestructive inspection of the eddy current probe 4, which is conducive to ensure more precise inspections and increase the detecting efficiency.

To sum up, the present invention takes advantages of the turntable transporting the objects and sequentially introducing them into the eddy current probe to have a nondestructive inspection and dispense the objects into defectives or non-defectives, thereby increasing the detecting speed. In addition, the present invention can also have an initial examination by the camera before guiding the objects into the eddy current probe, the initial flawless objects thus has dual detections, thereby promoting the inspection quality and efficiency.

While we have shown and described the embodiment in accordance with the present invention, it should be clear to those skilled in the art that further embodiments may be made without departing from the scope of the present invention.

I claim:

1. An inspecting apparatus with eddy current inspection comprising:
    a determining device;
    an inlet conveyer system for orientating and aligning objects;
    a turntable connecting to an exit of said inlet conveyer system and including a plurality of cutout grooves spaced around an outer periphery thereof to receive and position said objects therein;
    a shield board surrounding said turntable to prevent drops of said objects;
    an outlet conveyer system disposed by the side of said turntable so as to sequentially output said objects; and
    an eddy current probe being pivoted to an exit of said outlet conveyer system for receiving said objects and electrically communicated with said determining device; said eddy current probe further comprising:
    a detecting entrance for passing said objects therethrough;
    a detector disposed on an outer circumference of said detecting entrance and communicating with said determining device; and
    a braking assembly and a dispensing system respectively mounted on said detecting entrance; wherein, said braking assembly having a power motor, and a braking rod driven by said power motor and laterally mounted through said detecting entrance to pause movements of said objects, whereby said objects would temporarily contact with said detector under a nondestructive inspection; said dispensing system being located below said braking assembly so as to sort said objects into defectives or non-defectives based on analyses of said determining device.

2. The inspecting apparatus with eddy current inspection as claimed in claim 1, wherein, said output conveyer system substantially connects said turntable and said eddy current probe; said output conveyer system further provides with two guiding rails and a channel formed therebetween; said two guiding rails has ends thereof disposed below said turntable and the other ends thereof contacted with said inspecting entrance, thereby providing guidance for said objects to easily enter therein.

3. The inspecting apparatus with eddy current inspection as claimed in claim 1, wherein, a camera is mounted on said turntable and electrically connected to said determining device.

* * * * *